United States Patent [19]

Aberg et al.

[11] Patent Number: 5,677,346

[45] Date of Patent: Oct. 14, 1997

[54] TREATING URINARY INCONTINENCE USING (S)-DESETHYLOXYBUTYNIN

[75] Inventors: Gunnar Aberg, Westborough; John R. McCullough, Worcester; Yue Fang, Shrewsbury, all of Mass.

[73] Assignee: Sepracor, Inc., Marlborough, Mass.

[21] Appl. No.: 480,194

[22] Filed: Jun. 7, 1995

Related U.S. Application Data

[63] Continuation-in-part of Ser. No. 381,542, Jan. 31, 1995, Pat. No. 5,532,278.

[51] Int. Cl.$^6$ .......................... A61K 31/165; A61K 9/70
[52] U.S. Cl. .......................... 51/617; 514/310; 514/946; 424/449; 424/451; 424/464
[58] Field of Search .................... 514/617, 310, 514/946; 424/449, 451, 464

[56] References Cited

FOREIGN PATENT DOCUMENTS

| 902605 | 6/1985 | Belgium. |
| 94/206336 | 5/1994 | Japan .......................... A61K 9/70 |
| 940540 | 7/1961 | United Kingdom. |
| 92/20377 | 11/1992 | WIPO. |
| 95/09007 | 4/1995 | WIPO .......................... A61K 47/14 |

OTHER PUBLICATIONS

Lindeke et al. "Metabolism of Oxybutnin: Establishment of Desethyloxybutynin and Oxybutynin N–Oxide Formation in Rat Liver Preparations Using Deuterium Substitution and Gas Chromatographic Mass Spectrometric Analysis" *Biomedical Mass Spectrometry*, vol. 8, No. 10, 506–513 (1981).
Kasama et al. "Preparation of Substituted Glycolic acid 4–alkyl=amino–2–butynyl Esters as Antispasmodics and for Regulation of Urination" *Chemical Abstracts*, vol 113:23118k, 586 (1990).
Lish et al. "Oxybutynin—A Musculotropic Antispamodic Drug ... " *Arch. int. Pharmacodyn.* 156, 456–488 (1965).
Hock "Clinical Evaluation of Oxybutynin Chloride" *Current Therpapeutic Research* 9, 437–440 (1967).
Fredericks et al. "A Study of the Anticholinergic and Antispasmodic Activity of Oxybutynin ... " *Investigative Urology* 12, 317–319 (1975).
Nilvebrant et al. "Dicyclomine, Benzhexol and Oxybutynine Distinguish ... " *Europ. J. Pharmacol.* 123, 133–143 (1986).
Tonini et al. "Depressant action of oxybutynin on the contractility ... " *J. Pharm. Pharmacol.* 39, 103–107 (1986).

Kachur et al. "R and S Enantiomers of Oxybutynin: Pharmacological Effects ... " *J. Pharm. Exper. Ther.* 247, 867–872 (1988).
Noronha–Blob et al. "Muscarinic Receptors: Relationships Among Phosphoinositide ... " *J. Pharm. Exper. Ther.* 249, 843–851 (1989).
Noronha–Blob et al. "The Anticholinergic Activity of Agents Indicated for Urinary ... " *J. Pharm. Exper. Ther.* 251, 586–593 (1989).
Peterson et al. "In Vivo Cystometrogram Studies in Urethane–Anesthetized and Conscious Guinea Pigs" *J. Pharm. Methods* 21, 231–241 (1989).
Guarneri et al. "Effects of Oxybutynin, Terodiline, and Nifedipine ... " *Pharm. Research.* 24, 263–272 (1991).
Noronha–Blob et al. "Enantiomers of Oxybutynin: In Vitro Pharmacological Characterization ... " *J. Pharm. Exp. Ther.* 256, 562–567 (1990).
Lowe et al. "Effect of extracellular $Ca^{2+}$ on cholinergic, KCL and phorbol ester–mediated ... " *Eur. J. Pharm.* 195, 237–279 (1991).
Massad et al. "The Pharmacokinetics of Intravesical and Oral Oxybutynin Chloride" *J. Urology* 148, 595–597 (1992).
Angelico et al. "In Vivo Effects of Different Antispasmodic Drugs on the Rat Bladder Contractions" *J. Pharm. Methods* 27, 33–39 (1992).
Guarneri et al. "Effects of Drugs Used in the Therapy of Detrusor Hyperactivity. .. " *Pharm. Research* 27, 173–187 (1993).
Hughes et al. "Measurement of oxybutynin and its N–desethyl metabolite in plasma, and ... " *Xenobiotica* 22, 859–869 (1992).
Take et al. "Agents for the Treatment of Overactive Detrusor, III. Synthesis and ... " *Chem. Pharm. Bull.* 40, 1415–1423 (1992).
Cooley & Evain "Amine Dealkylations with Acyl Chlorides" *Synthesis* 1989, 1–7 (1989).

*Primary Examiner*—John W. Rollins
*Attorney, Agent, or Firm*—Heslin & Rothenberg, P.C.

[57] ABSTRACT

A method for treating urinary incontinence while avoiding concomitant liability of adverse effects associated with racemic oxybutynin is disclosed. The method comprises administering a therapeutically effective amount of (S)-oxybutynin, (S)-desethyloxybutynin or a pharmaceutically acceptable salt thereof, substantially free of the corresponding R enantiomer. Pharmaceutical compositions in the form of tablets and transdermal devices comprising (S)-oxybutynin or (S)-desethyloxybutynin and an acceptable carrier are also disclosed, as is a synthesis of desethyloxybutynin.

21 Claims, No Drawings

TREATING URINARY INCONTINENCE USING (S)-DESETHYLOXYBUTYNIN

CROSS-REFERENCE TO RELATED APPLICATIONS

This is a continuation-in-part of applicants' U.S. patent application Ser. No. 08/381,542, filed Jan. 31, 1995 now U.S. Pat. No. 5,532,278.

FIELD OF THE INVENTION

The invention relates to a method for treating urinary incontinence using optically pure (S)-oxybutynin and (S)-desethyloxybutynin (S-DEO), to pharmaceutical compositions containing optically pure (S)-oxybutynin or S-DEO, and to a process for preparing single enantiomers of DEO.

BACKGROUND OF THE INVENTION

Racemic oxybutynin is used therapeutically in the treatment of intestinal hypermotility and in the treatment of urinary incontinence due to detrusor instability. Racemic oxybutynin exerts a direct antispasmodic effect on smooth muscle and inhibits the action of acetylcholine on smooth muscle. It exhibits only one-fifth of the anticholinergic activity of atropine on the rabbit detrusor muscle, but four to ten times the antispasmodic activity. It is quite selective for muscarinic receptors in the presence of nicotinic receptors and as a result, no blocking effects are observed at skeletal neuromuscular junctions or autonomic ganglia.

Racemic oxybutynin relaxes bladder smooth muscle and, in patients with conditions characterized by involuntary bladder contractions, cystometric studies have demonstrated that racemic oxybutynin increases vesicle capacity, diminishes the frequency of involuntary contractions of the detrusor muscle, and delays the initial desire to void. It is therefore useful in the treatment and prevention of both incontinency and frequent voluntary urination. The efficacy of racemic oxybutynin in the bladder has been attributed to a combination of antimuscarinic, direct spasmolytic and local anesthetic effects on the detrusor smooth muscle. Because of the antimuscarinic activity of the racemic drug, xerostomia (dry mouth) and mydriasis (dilated pupils), which involve muscarinic cholinergic receptors, are very common side effects. In fact, at least one researcher has referred to the "inevitable symptoms of mydriasis, xerostomia, tachycardia, etc." that accompany the administration of racemic oxybutynin [Lish et al. Arch Int. Pharmacodyn. 156, 467–488 (1965), 481]. The high incidence of anticholinergic side effects (40 to 80%) often results in dosage reduction or discontinuation of therapy.

Pharmacological studies of the individual enantiomers have suggested that the R-enantiomer is the efficacious enantiomer. Noronha-Blob et al. [J. Pharmacol. Exp. Ther. 256, 562–567 (1991)] concluded that the cholinergic antagonism of racemic oxybutynin (measured in vitro by its affinity for $M_1$, $M_2$ and $M_3$ receptors subtypes and in vivo for diverse physiological responses) could be attributed mainly to the activity of the R-enantiomer. For all responses they found the rank order of potency of racemic oxybutynin and its enantiomers to be the same, namely, (R)-oxybutynin greater than or equal to racemic oxybutynin, which was much greater than (S)-oxybutynin, with (S)-oxybutynin being 1 to 2 orders of magnitude less potent than (R)-oxybutynin.

SUMMARY OF THE INVENTION

It has now been unexpectedly found that the substantially optically pure S enantiomer of oxybutynin and of its desethyl metabolite provide a superior therapy for the treatment of urinary incontinence.

Optically pure (S)-oxybutynin (S-OXY) and (S)-desethyloxybutynin (S-DEO) provide this treatment while substantially reducing the adverse effects that primarily arise from anticholinergic activity and that are associated with the administration of racemic oxybutynin. These include, but are not limited to, xerostomia, mydriasis, drowsiness, nausea, constipation, palpitations and tachycardia. The amelioration of cardiovascular side effects of racemic oxybutynin, such as tachycardia and palpitations, by the administration of (S)-oxybutynin or S-DEO is of particular therapeutic value.

The active compounds of these compositions and methods are optical isomers of oxybutynin and desethyloxybutynin. The preparation of racemic oxybutynin is described in British Patent Specification 940,540. Chemically, the active compounds are (1) the S enantiomer of 4-(diethylamino)-2-butynyl α-cyclohexyl-α-hydroxybenzeneacetate also known as 4-(diethylamino)-2-butynyl phenylcyclohexylglycolate, and hereinafter referred to as oxybutynin; and (2) the S enantiomer of 4-(ethylamino)-2-butynyl α-cyclohexyl-α-hydroxybenzeneacetate, and hereinafter referred to as desethyloxybutynin. The generic name given to the hydrochloride salt of racemic oxybutynin by the USAN Council is oxybutynin chloride; it is sold under the trade name of Ditropan®. The isomer of oxybutynin having the S absolute stereochemistry (Registry Number 119618-22-3) is dextrorotatory, and is shown in Formula I:

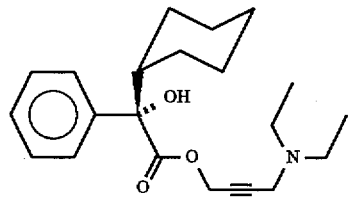

The S enantiomer of desethyloxybutynin is shown in Formula II:

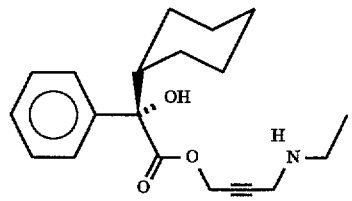

The synthesis of (S)-oxybutynin has been described [Kachur et al. J. Pharmacol. Exp. Ther. 247, 867–872 (1988)], but (S)-oxybutynin itself is not presently commercially available. All of the clinical results that have been reported have been obtained with the racemic mixture, although the pharmacology of the individual enantiomers has been described in guinea pigs and rats [see Kachur et al. J. Pharmacol. Exp. Ther. 247, 867–872 (1988) and Noronha-Blob et al. J. Pharmacol. Exp. Ther. 256, 562–567 (1991)]. (S)-Desethyloxybutynin has not been previously described; its synthesis is carried out according to the method described below.

In one aspect the invention relates to a method for treating urinary incontinence while avoiding concomitant liability of adverse effects, which comprises administering to a human in need of such treatment a therapeutically effective amount of (S)-oxybutynin, (S)-desethyloxybutynin or a pharmaceutically acceptable salt of either, substantially free of the corresponding R enantiomer. The term "substantially free of its R enantiomer" as used herein means that the compositions contain at least 90% by weight of (S)-oxybutynin or (S)-desethyloxybutynin and 10% by weight or less of (R)-oxybutynin or (R)-desethyloxybutynin.

In a more preferred embodiment, the compositions contain at least 99% by weight of the S enantiomer and 1% or less of the R enantiomer. The substantially optically pure (S)-oxybutynin or (S)-desethyloxybutynin may be administered parentally, rectally, intravesically, transdermally, orally or by aerosol, orally and transdermally being preferred, at a rate of about 1 mg to about 100 mg per day.

In another aspect, the invention relates to a pharmaceutical unit dosage form in the form of a tablet or capsule comprising a therapeutically effective amount of (S)-oxybutynin, (S)-desethyloxybutynin or a pharmaceutically acceptable salt of either, substantially free of the corresponding R stereoisomer, and a pharmaceutically acceptable carrier. The tablet or capsule preferably contains from 0.5 to 25 mg of (S)-oxybutynin or (S)-desethyloxybutynin and is prepared by conventional methods, well-known in the art. The invention also relates to a dosage form in the form of a transdermal device. The transdermal administration is improved by the inclusion of a permeation enhancer in the transdermal delivery device, for example as described in PCT application WO 92/20377.

In a further aspect the invention relates to a process for preparing desethyloxybutynin, preferably a single enantiomer of DEO, most preferably S-DEO, comprising the steps of, first, reacting methyl α-cyclohexyl-α-hydroxybenzeneacetate with 4-[N-ethyl-(4-methoxyphenyl)methylamino]-2-butyn-1-ol in the presence of an anhydrous base to produce 4-[N-ethyl-(4-methoxyphenyl)methylamino]-2-butynyl α-cyclohexyl-α-hydroxybenzeneacetate; and then sequentially with a carbonochloridate and methanol to produce 4-(ethylamino)-2-butynyl α-cyclohexyl-α-hydroxybenzeneacetate (desethyloxybutynin). The process may additionally comprise reacting N-ethyl-4-methoxybenzenemethanamine with 2-propyn-1-ol and formaldehyde or a formaldehyde equivalent in the presence of a copper(I) salt to produce the 4-[N-ethyl-(4-methoxyphenyl)methylamino]-2-butyn-1-ol needed for the first step.

DETAILED DESCRIPTION OF THE INVENTION

The S enantiomers of oxybutynin and DEO may be obtained by resolution of the intermediate mandelic acid followed by esterification. The esterification can be carried out as described by Kachur et al. (op. cit.) for OXY or by the improved method depicted in Scheme A below for S-DEO.

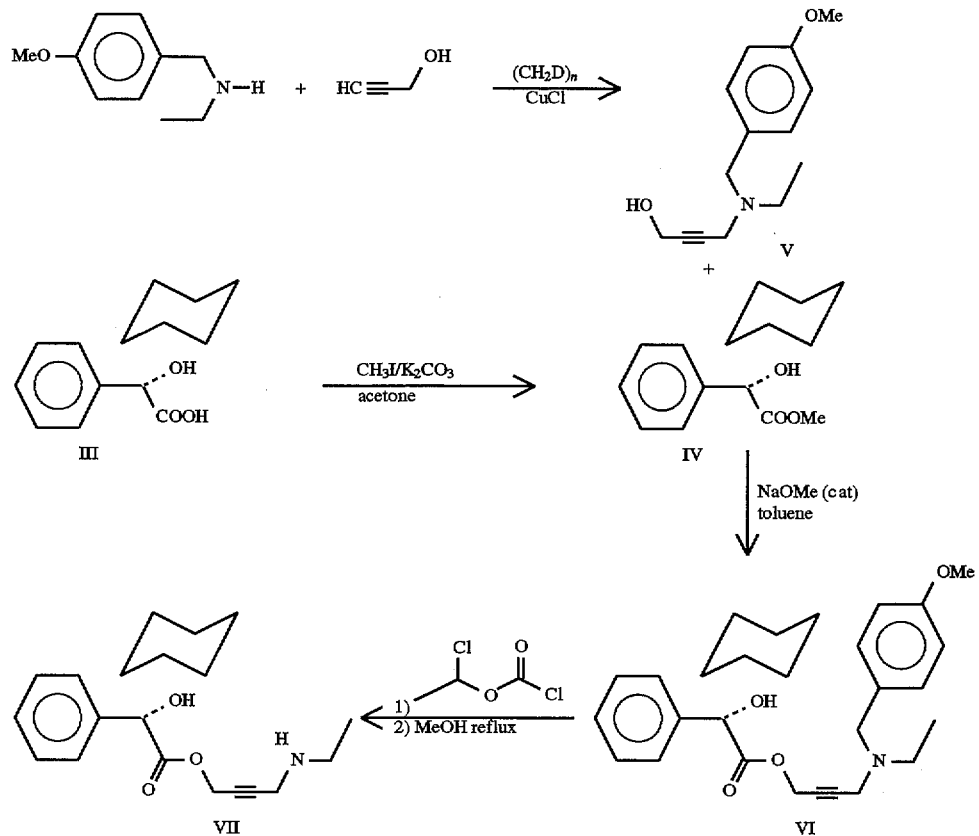

The graphic representations of racemic, ambiscalemic and scalemic or enantiomerically pure compounds used herein are taken from Maehr *J. Chem. Ed.* 62, 114–120 (1985). Thus, solid and broken wedges (such as shown in formula I) are used to denote the absolute configuration of a chiral element; wedge outlines and dotted or broken lines (such as shown in formula III) denote enantiomerically pure compounds of indeterminate absolute configuration.

The overall process for DEO involves:

(a) reacting N-ethyl-4-methoxybenzenemethanamine with 2-propyn-1-ol and paraformaldehyde in an inert solvent in the presence of cuprous chloride to produce 4-[N-ethyl-(4-methoxyphenyl)methylamino]-2-butyn-1-ol (V);

(b) reacting a single enantiomer of methyl α-cyclohexyl-α-hydroxybenzeneacetate (IV) with 4-[N-ethyl-(4-methoxyphenyl)methylamino]-2-butyn-1-ol (V) in the presence of a catalytic amount of sodium methoxide in toluene to produce a single enantiomer of 4-[N-ethyl-(4-methoxyphenyl)methylamino]-2-butynyl α-cyclohexyl-α-hydroxybenzeneacetate (VI); and (c) reacting 4-[N-ethyl-(4-methoxyphenyl)methylamino]-2-butynyl α-cyclohexyl-α-hydroxybenzeneacetate (VI) sequentially with α-chloroethyl carbonochloridate in dichloroethane, followed by methanol to produce a single enantiomer of DEO (VII).

The process is obviously applicable to producing racemic DEO from racemic methyl α-cyclohexyl-α-hydroxybenzeneacetate as well. Paraformaldehyde is used as a convenient source of formaldehyde, but it can be replaced by any source of formaldehyde, as is well known in the art. Similarly α-chloroethyl carbonochloridate is used for the dealkylation, but other carbonochloridates (e.g. vinyl) could be employed.

Alternatively, the S enantiomers of OXY and DEO may be obtained by the resolution of racemic oxybutynin or DEO using conventional means such as fractional crystallization of diastereomeric salts with chiral acids. Other standard methods of resolution known to those skilled in the art, including, but not limited to, simple crystallization and chromatography on a chiral substrate can also be used.

The magnitude of a prophylactic or therapeutic dose of (S)-oxybutynin or S-DEO in the acute or chronic management of disease will vary with the severity and nature of the condition to be treated and the route of administration. The dose and perhaps the dose frequency will also vary according to the age, body weight and response of the individual patient. In general, the total daily dose range for (S)-oxybutynin or S-DEO for the conditions described herein is from about 1 mg to about 100 mg in single or divided doses, preferably in divided doses. In managing the patient, the therapy should be initiated at a lower dose, perhaps at about 0.25 mg to about 25 mg, and increased up to about 100 mg depending on the patient's global response. It is further recommended that patients over 65 years and those with impaired renal or hepatic function initially receive low doses and that they be titrated based on individual response(s) and blood level(s). It may be necessary to use dosages outside these ranges in some cases, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat incontinence but insufficient to cause adverse effects" are encompassed by the above-described dosage amounts and dose frequency schedule.

Any suitable route of administration may be employed for providing the patient with an effective dosage of (S)-oxybutynin or S-DEO. For example, oral, rectal, parenteral (subcutaneous, intramuscular, intravenous), transdermal, aerosol and like forms of administration may be employed. Additionally, the drug may be administered directly into the bladder through the urethra, as described for racemic oxybutynin by Massad et al. [J. Urol. 148, 595–597 (1992)]. Dosage forms include tablets, troches, dispersions, suspensions, solutions, capsules, transdermal delivery systems, and the like.

The pharmaceutical compositions of the present invention comprise (S)-oxybutynin or S-DEO as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The hydrochloride has particular utility and was, in fact, the salt used in the studies described below.

The compositions of the present invention include suspensions, solutions, elixirs, or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations.

Because of their ease of administration, tablets and capsules represent one of the more advantageous oral dosage unit forms, in which case solid pharmaceutical carriers are employed. If desired, tablets may be coated by standard aqueous or nonaqueous techniques.

In addition to the common dosage forms set out above, the compounds of the present invention may also be administered by controlled release means and delivery devices such as those described in U.S. Pat. Nos.: 3,845,770; 3,916,899; 3,536,809; 3,598,123; and 4,008,719, and PCT application WO 92/20377, the disclosures of which are hereby incorporated by reference.

Pharmaceutical compositions of the present invention suitable for oral administration may be presented as discrete units such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation, just as is known for the racemic mixture.

The surprising utility of the S enantiomer of both OXY and DEO has been established by the following studies.

ENANTIOMERS OF OXYBUTYNIN

Binding of (R)- and (S)-Oxybutynin to Human $M_1$, $M_2$, $M_3$ and $M_4$ Muscarinic Receptor Subtypes

MATERIALS AND METHODS

The experiments were carried out on membranes prepared from SF9 cells infected with baculovirus to express the human recombinant $M_1$, $M_2$, $M_3$ and $M_4$ muscarinic receptor subtypes.

Binding Assays

TABLE 1

| Receptor | Radioligand | Conc. | Non-specific | Incubation | Reference Compound |
|---|---|---|---|---|---|
| $M_{1H}$ | [$^3$H]pirenzepine | 2 nM | atropine (1 µM) | 60 min 27° C. | pirenzepine |
| $M_{2H}$ | [$^3$H]AF-DX 384 | 2 nM | atropine (1 µM) | 60 min 27° C. | methoctramine |
| $M_{3H}$ | [$^3$H]4-DAMP | 0.8 nM | atropine (1 µM) | 60 min 27° C. | 4-DAMP |
| $M_{4H}$ | [$^3$H]4-DAMP | 0.3 nM | atropine ( µM) | 60 min 27° C. | 4-DAMP |

Following incubation, the assays were rapidly filtered under vacuum through GF/B glass fiber filters (Whatman) and washed with an ice-cold buffer using a Brandel Cell Harvester. Bound radioactivity was determined with a liquid scintillation counter (LS 6000, Beckman) using a liquid scintillation cocktail (Formula 99, DuPont NEN).

Experimental protocol

The compounds were tested on each receptor at 10 concentrations in duplicate to obtain competition curves. In each experiment, the reference compound for the receptor under investigation was simultaneously tested at 8 concentrations in duplicate to obtain a competition curve in order to validate this experiment.

Analysis and expression of results

The specific radioligand binding of each receptor was defined as the difference between total binding and nonspecific binding determined in the presence of an excess of unlabelled ligand. $IC_{50}$ values (concentrations required to inhibit 50% of specific binding) were determined by non linear regression analysis of the competition curves. These parameters were obtained by curve fitting using Sigmaplot™ software. $IC_{50}$ for R- and S-OXY are given in Table 2.

TABLE 2

Binding of R-oxybutynin and S-oxybutynin to human muscarinic subtypes M1–M4

| Receptor | R-OXY $IC_{50}$ (nM) | S-OXY $IC_{50}$ (nM) | Ref. Compound | $IC_{50}$ (nM) |
|---|---|---|---|---|
| M1 | 0.99 | 47.6 | Pirenzepine | 11.9 |
| M2 | 9.9 | 178 | Methoctramine | 14.6, |
| M3 | 1.8 | 149 | 4-DAMP | 1.6 |
| M4 | 1.2 | 100 | 4-DAMP | 0.87 |

These results indicate that S-OXY has less affinity for muscarinic receptor subtypes than does R-OXY.

Binding of (R)- and (S)-Oxybutynin to Calcium channels

MATERIALS AND METHODS

Binding assays

Binding assays were performed using the following methods:

TABLE 3

| Receptors | Membranes | Reference Compounds | References |
|---|---|---|---|
| Ca channel (T + L, diltiazem site) | rat cerebral cortex | diltiazem | Schoemaker and Langer (1985) |

TABLE 3-continued

| Receptors | Membranes | Reference Compounds | References |
|---|---|---|---|
| Ca channel (T + L, verapamil site) | rat cerebral cortex | D600 | Reynolds et al (1986) |

The experiment conditions were:

TABLE 4

| Receptors | Ligands | Concentrations | Non-specific | Incubation |
|---|---|---|---|---|
| Ca channel (T + L, diltiazem site) | [$^3$H] diltiazem | 5 nM | diltiazem (10 µM) | 120 min 25° C. |
| Ca channel (T + L, verapamil site) | [$^3$H]D 888 | 0.5 nM | D 600 (10 µM) | 60 min 22° C. |

Following incubation, the assays were rapidly filtered under vacuum through GF/B or GF/C glass fiber filters (Whatman) and washed with an ice-cold buffer using a Brandel Cell Harvester. Bound radio-activity was determined with a liquid scintillation counter (LS6000, Beckman) using a liquid scintillation cocktail (Formula 989, DuPont NEN).

Experimental Protocols

The compounds were tested in duplicate on each receptor at a concentration of $10^{-5}$M. In each experiment, the reference compound for the receptor under investigation was simultaneously tested at 8 concentrations in duplicate to obtain a competition curve in order to validate this experiment.

Analysis and expression of results

The specific radioligand binding of each receptor was defined as the difference between total binding and nonspecific binding determined in the presence of an excess of unlabelled ligand. Mean values, expressed as a percentage of inhibition of specific binding, are presented in Table 5. $IC_{50}$ values (concentration required to inhibit 50% of specific binding) were determined by non linear regression analysis of their competition curves. These parameters were obtained by curve fitting using Sigmaplot™ software.

TABLE 5.

Binding of R-oxybutynin and S-oxybutynin to calcium channels

[Inhibition (in %) of diltiazem and verapamil binding to calcium channel receptors.]

| Receptor | R-OXY ($10^{-5}$M) | S-OXY ($10^{-5}$M) | Ref. Compound | $IC_{50}$(nM) |
|---|---|---|---|---|
| Calcium (diltiazem) | 86 | 59 | diltiazem | 55.8 |
| Calcium (verapamil) | 86 | 68 | D600 | 36.4 |

These results indicate that S-OXY has calcium entry blocking activity similar to R-OXY.

ENANTIOMERS OF DESETHYLOXYBUTYNIN

The major metabolite of racemic oxybutynin is RS-desethyl oxybutynin (DEO). The R and S enantiomers of DEO have not been described, and the antispasmodic and calcium entry blocking activities of the individual enantiomers, R- and S-DEO, were, prior to our studies, unknown. We have synthesized these enantiomers and have studied their antimuscarinic, spasmolytic and calcium entry blocking effects in models of receptor binding and bladder function. We have found that each enantiomer of the metabolite retains the relative pharmacological profile of its "parent" oxybutynin enantiomer.

Binding at Muscarinic Receptor Subtypes

The percent inhibition of specific radioligand binding induced by three concentrations of each compound (R-, S-, and RS-DEO) was tested at cloned human muscarinic receptor subtypes (M1–M4), as described above for the enantiomers of oxybutynin. The tables below (Tables 6 and 7) give the percent inhibition at each subtype. In addition, $IC_{50}$ values were determined for $M_1$ and $M_2$ human receptor subtypes and are presented in Table 6.

TABLE 6

| | $M_{1H}$ | | | | $M_{2H}$ | | | |
|---|---|---|---|---|---|---|---|---|
| | $10^{-9}M$ | $10^{-7}M$ | $10^{-5}M$ | $IC_{50}$ (nM) | $10^{-9}M$ | $10^{-7}M$ | $10^{-5}M$ | $IC_{50}$ (nM) |
| R-DEO | 63 | 100 | 100 | 1.2 | 21 | 97 | 102 | 14.7 |
| S-DEO | — | 82 | 101 | 25.4 | — | 36 | 101 | 177 |
| RS-DEO | 43 | 100 | 100 | 1.8 | — | 94 | 99 | 7.0 |

TABLE 7

| | $M_{3H}$ | | | $M_{4H}$ | | |
|---|---|---|---|---|---|---|
| | $10^{-9}M$ | $10^{-7}M$ | $10^{-5}M$ | $10^{-9}M$ | $10^{-7}M$ | $10^{-5}M$ |
| R-DEO | 58 | 100 | 100 | 58 | 100 | 99 |
| S-DEO | — | 63 | 99 | — | 43 | 99 |
| RS-DEO | 36 | 99 | 101 | 34 | 99 | 95 |

These results indicate that S-DEO has less affinity for muscarinic receptor subtypes than either R- or racemic DEO.

Binding at Calcium Channels

The percent inhibition of specific radioligand binding induced by each compound (R-, S-, and RS-DEO) was tested at the diltiazem and verapamil sites of the L-type calcium channel. The results are shown in Table 8.

TABLE 8

| Receptor | R-Deo $10^{-5}M$ | S-DEO $10^{-5}M$ | RS-DEO $10^{-5}M$ |
|---|---|---|---|
| Calcium (diltiazem) | 86 | 72 | 88 |
| Calcium (verapamil) | 96 | 76 | 89 |

These results indicate that S-DEO has calcium entry blocking activity similar to that of R- and racemic DEO.

Functional Characterization of Antimuscarinic/ Antispasmodic Activity

The effects of R-, S- and RS-Oxybutynin (OXY) and of R-, S-, and RS-DEO were studied in an in vitro model of bladder function. As described below, isolated strips of guinea pig bladder smooth muscle were mounted in a tissue bath and contracted either with the muscarinic agonist carbachol or with increasing concentrations of external potassium.

MATERIALS AND METHODS

Bladder strips. Experiments were performed using methods similar to those described by Kachur et al, 1988 and Noronha-Blob and Kachur, 1991. Strips of tissue (approximately 10 mm long and 1.5 mm wide) were removed from the body of the urinary bladder of male Hartley guinea pigs weighing 400–600 g. (Elm Hill Breeding Laboratories, Chelmsford, Mass.). The tissues were suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. They were maintained at 37.5° C. Contractions were recorded with isometric transducers (Model FT-10) and an ink-writing polygraph (Model 7) (Astro-Med, Inc., Grass Instrument Div., West Warwick, R.I.). A resting tension of 0.5 grams was maintained on all tissues at all times.

In each experiment up to seven strips were removed from a single bladder, suspended in individual tissue chambers and allowed to equilibrate with the bathing solution for one hour before proceeding with the experiment.

Carbachol-induced contractions. One series of experiments focused on the anticholinergic actions of oxybutynin. In these experiments, in order to assess the viability of each tissue and to serve as a frame of reference, contractions of each strip of tissue were recorded initially in response to exposure to tissue medium in which the NaCl was replaced by KCl to yield a concentration of 137.7 mM KCl in the medium. This was followed by return to the standard medium, and then by exposures to progressively increasing concentrations of carbachol, with separate exposures to each concentration only until the peak response had been recorded. Then, leaving one strip untreated and/or one strip exposed to 17 mM ethanol to serve as control tissue(s), the remaining strips each were exposed for one hour to one concentration of an antagonist. The ethanol controls were used when, because of poor solubility, stock solutions of test substances had to be prepared in ethanol, as a result of which the tissue baths experienced an effective concentration of 17 mM ethanol. Finally, the responses to increasing concentrations of carbachol followed by exposure to 137.7 mM KCl were recorded a second time.

Potassium-induced contractions. A second series of experiments focused on the spasmolytic action of the substances being studied. Contractions were recorded in response to sequentially increasing the concentration of potassium in the medium.

Data analysis. To determine whether antagonists decreased the peak response to agonists, the peak tension developed by each strip during the second set of determinations was expressed as a percent of the peak tension developed during the first concentration-effect determination. Then, for each antagonist the resultant data were analyzed for treatment-related differences by one-way analysis of variance (ANOVA). Since only one concentration of antagonist was studied in each strip of bladder, the procedures of Arunlakshana and Schild (1959) were used in modified form to estimate the pA2 and slope of the Schild regression. First, the concentrations of agonist producing a half-maximal response (the $EC_{50}$) was estimated for each strip from the second set of concentration-effect data. The $EC_{50}$ was obtained from linear regression lines fit to the logarithm of the concentration of drug and the responses bracketing the half maximum level of response. For each drug-treated strip, a "concentration ratio" (CR) was calculated as the ratio of the $EC_{50}$ of the treated tissue divided by the $EC_{50}$ of the untreated tissue. For each experiment where two or more strips were exposed to the same chemical but at different concentrations, the logarithm of this ratio minus one [i.e., log (CR-1)] was plotted against the logarithm of the concentration of antagonist to which the strip had been exposed to produce "Schild plots". A regression analysis relating log(CR-1) to the logarithm of the concentration of the antagonist was employed to estimate the pA2 and the slope of the regression line. Finally, experiments were grouped by chemical and the mean ± S.E. of the pA2 and slope were calculated. The 95% confidence limits (CL) for the slope were estimated from its S.E. using standard methods. For experiments in which only one strip was exposed to a given chemical, a pKD was calculated as (concentration of antagonist)/(CR-1) and the negative logarithm of the KD was then pooled with the pA2 values to yield an expanded set of pA2 values.

Results

The effects of racemic oxybutynin and DEO and their respective enantiomers on carbachol-induced contraction are summarized in Table 9 below. Values given are the summary of Schild analyses which gives pA2 values [mean ± SE] and slope [mean ± SE].

TABLE 9

| Antagonist | No. of expts. | pA2 | Slope |
|---|---|---|---|
| R-OXY | 4 | 8.80 ± 0.27 | 1.28 ± 0.26 |
| S-OXY | 4 | 7.09 ± 0.13 | 1.13 ± 0.17 |
| RS-OXY | 5 | 8.81 ± 0.29 | 1.34 ± 0.15 |
| R-DEO | 4 | 9.04 ± 0.32 | 1.16 ± 0.11 |
| S-DEO | 4 | 7.31 ± 0.35 | 0.87 ± 0.11 |
| RS-DEO | 4 | 8.55 ± 0.32 | 1.35 ± 0.25 |

These results indicate that both S-OXY and S-DEO are less potent antagonists of bladder muscarinic receptors than are R- and racemic OXY and R- and racemic DEO.

The effects of racemic oxybutynin and its enantiomers on potassium-induced contraction are summarized in Table 10 below. (Values given are the magnitude of contraction induced by 137.7 mM K+ after 60 min exposure to compound divided by the magnitude of contraction induced before exposure to drug.)

TABLE 10

| Antagonist | Mean % pretreatment ± SE (n = 3) |
|---|---|
| R-OXY | 32 ± 8* |
| S-OXY | 26 ± 9* |
| RS-OXY | 20 ± 1* |
| R-DEO | 36 ± 5* |
| S-DEO | 42 ± 5* |
| RS-DEO | 47 ± 8* |

*Significantly different from corresponding value for untreated tissues ($p < 0.01$)

These results indicate that oxybutynin and its enantiomers and desethyl oxybutynin and its enantiomers are equipotent as bladder smooth muscle spasmolytics.

CONCLUSIONS

While it is well known that the normal emptying of the bladder is mediated through cholinergic mechanisms, the bladder instability that is seen in patients suffering from incontinence appears to be related to non-cholinergic contractions of the bladder. Andersson et al. [*Neurourol Urodyn* 5, 579–586 (1986)] have shown in animals that the atropine-resistant detrusor muscle is highly sensitive to calcium antagonists.

The study of the receptor binding affinities of (R)- and (S)-oxybutynin to the receptor sites for the calcium channel blockers diltiazem and verapamil described above allows one to conclude that S-oxybutynin and (S)-desethyloxybutynin have therapeutic effects on involuntary micturition, while (unlike the R-isomers and the racemates) having very little effect on the normal voiding mechanism. Both also exhibit significantly decreased anticholinergic side effects as compared with the corresponding R-isomer and racemate. The avoidance of cardiovascular side effects that arise from the anticholinergic action of racemic oxybutynin is of particular note. We conclude that S-oxybutynin and S-desethyl oxybutynin are effective medicaments for the treatment of urinary incontinence in humans with greatly reduced side effects over the racemates or the pure R-enantiomers.

Methyl (R)-α-cyclohexyl-α-hydroxybenzeneacetate (IV)

To a mixture of (R)-α-cyclohexyl-α-hydroxybenzeneacetic acid (III) (12.2 g, 52.1 mmol) and $K_2CO_3$ (10.8 g, 78.2 mmol) in 100 mL of acetone was added methyl iodide (MeI) (13.0 mL, 208 mmol) dropwise at 0° C. (ice bath). After the addition (ca. 1 h) of MeI, the reaction mixture was stirred at room temperature overnight. The mixture was filtered through a pad of Celite and rinsed with acetone twice. The filtrate was concentrated to give a white slurry which was diluted with water and extracted with heptane. The combined extracts were washed with water, brine, dried and concentrated to give the product (R)-IV (11.9 g, 92% yield) as a white solid.

Methyl (S)-α-cyclohexyl-α-hydroxybenzeneacetate (IV):

Following the same procedure as above, (S)-IV (11.2 g, 100% yield) was obtained as a white solid from (S)-III (10.6 g, 45.3 mmol).

4-[N-Ethyl-(4-methoxyphenyl)methylamino]-2-butynyl (R)-α-cyclohexyl-α-hydroxybenzeneacetate (VI):

To a solution of (R)-IV(11.9 g, 47.7 mmol) and 4-[N-ethyl-(4-methoxyphenyl)methylamino]-2-butyn-1-ol (V) (9.30 g, 39.9 mmol) in 120 mL of toluene was added NaOMe (0.222 g, 4.11 mmol). The reaction mixture was stirred at reflux for 5 h and a total of 6 mL of the solvent was removed by Dean-Stark apparatus. The reaction mixture was cooled to room temperature, diluted with ethyl acetate, washed with water, brine, dried and concentrated. The residue was chromatographed on silica gel (elution with 1%, 2.5% and then 5% MeOH in $CH_2Cl_2$) to afford the product (R)-VI(14.1 g, 79% yield) as an oil.

4-[N-Ethyl-(4-methoxyphenyl)methylamino]-2-butynyl (S)-α-cyclohexyl-α-hydroxybenzeneacetate (VI):

Following the same procedure as above, (S)-VI(4.24 g, 58% yield) was obtained as an oil from (S)-IV(4.07 g, 16.4 mmol) and V (4.24 g, 18.2 mmol).

Racemic 4-[N-Ethyl-(4-methoxyphenyl)methylamino]-2-butynyl (S)-α-cyclohexyl-α-hydroxybenzene-acetate:

Following the same procedure as above, the racemic precursor to DEO (2.05 g, 43% yield) was obtained as an oil from racemic IV (2.98 g, 12.0 mmol) and V (2.48 g, 10.6 mmol).

4-(Ethylamino)-2-butynyl (R)-α-cyclohexyl-α-hydroxybenzeneacetate hydrochloride salt (VII)-HCl:

A solution of (R)-VI (14.0 g, 31.2 mmol) and α-chloroethyl carbonochloridate (4.0 mL, 37.4 mmol) in 1,2-dichloroethane was stirred at reflux for 1 h. After cooling, the reaction mixture was concentrated and 200 mL of MeOH was added to the residue. The reaction mixture was stirred at reflux for 20 min and cooled to room temperature. The mixture was concentrated and the residue was chromatographed on silica gel (elution with 1% and then 50% MeOH in $CH_2Cl_2$) and then triturated with ether to afford the product (R)-VII-HCl (8.93 g, 87% yield) as a tan solid. This tan solid was further purified by recrystallization from $EtOH/Et_2O$ and by sequential treatment with 10% aqueous $K_2CO_3$ and EtOAc, activated carbon, and a solution of 1N HCl in ether to give (R)-DEO-HCl (6.44 g) as an off-white solid.

4-(Ethylamino)-2-butynyl (S)-α-cyclohexyl-α-hydroxybenzeneacetate hydrochloride salt (VII)-HCl:

Following the same procedure as above, (S)-DEO-HCl (5.27g, 57% yield) was obtained as an off-white solid from (S)-VI (11.4g, 25.4 mmol).

Racemic 4-(Ethylamino)-2-butynyl α-cyclohexyl-α-hydroxybenzeneacetate hydrochloride salt:

Following the same procedure as above, (±)-DEO-HCl (0.63 g) was obtained as an off-white solid from (±) precursor (2.28 g, 5.08 mmol).

S-Oxybutynin may be prepared by the same route, substituting 4-(diethylamino)-2-butyn-1-ol for the protected intermediate V.

The 4-[N-ethyl-(4-methoxyphenyl)methylamino]-2-butyn-1-ol (V) used as an intermediate is synthesized as follows:

N-Ethyl-4-methoxybenzenemethanamine:

To a mixture of anisaldehyde (15.6 g, 115 mmol) and ethylamine (2.0M in THF, 87 mL, 174 mmol) in 1,2-dichloroethane (450 mL) was added glacial acetic acid (10.0 mL, 174 mmol) under nitrogen atmosphere. The reaction mixture was stirred at room temperature for 30 min and then cooled to 0° C. with ice bath. $NaBH(OAc)_3$ (36.9 g, 174 mmol) was added portionwise and the reaction mixture was stirred at room temperature overnight. The mixture was concentrated and the residue was diluted with a basic solution (10 g NaOH in 100 mL of water) to make the solution slightly basic. This aqueous layer was extracted with ether. The combined extracts were washed with water, brine, dried and concentrated. The residue was chromatographed on silica gel (elution with 5% MeOH in $CH_2Cl_2$ and then 50% MeOH in $CH_2Cl_2$ containing 4% $Et_3N$) to afford the product (11.2 g, 59% yield) as an oil.

4-[N-ethyl-(4-methoxyphenyl)methylamino]-2-butyn-1-ol (v):

A mixture of N-ethyl-4-methoxybenzenemethanamine (13.3 g, 80.6 mmol), paraformaldehyde (3.63 g), propargyl alcohol (6.33 g, 113 mmol) and CuCl (0.311 g) in 350 mL of 1,4-dioxane was stirred at reflux for 30 min. The reaction mixture was cooled to room temperature and concentrated. The residue was diluted with 200 mL of 50% $NH_4OH$ and extracted with EtOAc. The combined extracts were washed with water, brine, dried and concentrated. The residue was chromatographed on silica gel (elution with 2.5% MeOH in $CH_2Cl_2$ and then 5% MeOH in $CH_2Cl_2$) to afford the product V (15.1 g, 81% yield) as an oil.

We claim:

1. A method for treating urinary incontinence while avoiding concomitant liability of adverse effects, which comprises administering to a human in need of such treatment a therapeutically effective amount of (S)-desethyloxybutynin or a pharmaceutically acceptable salt thereof, substantially free of its (R) enantiomer.

2. The method of claim 1 wherein (S)-desethyloxybutynin is administered by inhalation or by parenteral, transdermal, rectal or oral administration.

3. The method of claim 2 wherein the amount of (S)-desethyloxybutynin or a pharmaceutically acceptable salt thereof administered is from about 1 mg to about 100 mg per day.

4. The method according to claim 1 wherein (S)-desethyloxybutynin, or pharmaceutically acceptable salt thereof, is administered orally.

5. The method according to claim 1 wherein (S)-desethyloxybutynin, or pharmaceutically acceptable salt thereof, is administered transdermally.

6. The method of claim 1, wherein (S)-desethyloxybutynin, or a pharmaceutically acceptable salt thereof, is administered parenterally.

7. The method of claim 6 wherein (S)-desethyloxybutynin, or a pharmaceutically acceptable salt thereof, is administered intravenously.

8. The method of claim 6 wherein (S)-desethyloxybutynin, or a pharmaceutically acceptable salt thereof, is administered subcutaneously.

9. The method of claim 6 wherein (S)-desethyloxybutynin, or a pharmaceutically acceptable salt thereof, is administered intramuscularly.

10. A pharmaceutical unit dosage form in the form of a tablet or capsule which comprises a therapeutically effective amount of (S)-desethyloxybutynin, or a pharmaceutically acceptable salt thereof, substantially free of its (R) stereoisomer, and a pharmaceutically acceptable carrier.

11. A pharmaceutical unit dosage form according to claim 10 comprising from 0.5 to 25 mg of (S)-desethyloxybutynin.

12. A pharmaceutical dosage form in the form of a transdermal delivery device which comprises a therapeutically effective amount of (S)-desethyloxybutynin, or a pharmaceutically acceptable salt thereof, substantially free of its (R) stereoisomer, and a pharmaceutically acceptable carrier.

13. A pharmaceutical dosage form according to claim 12 wherein said pharmaceutically acceptable carrier comprises a permeation enhancer.

14. The pharmaceutical unit dosage form of claim 10 wherein said table or capsule is formulated for controlled release upon administration.

15. A process for preparing desethyloxybutynin comprising the steps of:

(a) reacting methyl α-cyclohexyl-α-hydroxybenzeneacetate with 4-[N-ethyl-(4-methoxyphenyl)methylamino]-2-butyn-1-ol in the presence of an anhydrous base to produce 4-[N-ethyl-(4-methoxyphenyl)methylamino]-2-butynyl α-cyclohexyl-α-hydroxybenzeneacetate; and (b) reacting said 4-[N-ethyl-(4-methoxyphenyl) methylamino]-2-butynyl α-cyclohexyl-α-hydroxybenzeneacetate sequentially with a carbonochloridate and methanol to produce 4-(ethylamino)-2-butynyl α-cyclohexyl-α-hydroxybenzeneacetate.

16. A process according to claim 15 comprising the additional step of reacting N-ethyl-4-methoxybenzenemethanamine with 2-propyn-1-ol and formaldehyde or a formaldehyde equivalent in the presence of a copper(I) salt to produce 4-[N-ethyl-(4-methoxyphenyl) methylamino]-2-butyn-1-ol.

17. A process according to claim 18 comprising:

(a) reacting N-ethyl-4-methoxybenzenemethanamine with 2-propyn-1-ol and paraformaldehyde in an inert solvent in the presence of cuprous chloride to produce 4-[N-ethyl-(4-methoxyphenyl)methylamino]-2-butyn-1-ol;

(b) reacting methyl α-cyclohexyl-α-hydroxybenzeneacetate with said 4-[N-ethyl-(4- methoxyphenyl)methylamino]-2-butyn-1-ol in the presence of sodium methoxide in toluene to produce 4-[N-ethyl-(4-methoxyphenyl)methylamino]-2-butynyl α-cyclohexyl-α-hydroxybenzeneacetate; and (c) reacting said 4-[N-ethyl-(4-methoxyphenyl) methylamino]-2-butynyl α-cyclohexyl-α-hydroxybenzeneacetate sequentially with α-chloroethyl carbonochloridate in dichloroethane, followed by methanol to produce 4-(ethylamino)-2-butynyl α-cyclohexyl-α-hydroxybenzeneacetate (desethyloxybutyin).

18. A process according to claim 15 wherein said methyl α-cyclohexyl-α-hydroxybenzeneacetate employed in step (a) contains an excess of one enantiomer over its opposite enantiomer, thereby producing desethyloxybutynin enriched in a single enantiomer.

19. A process according to claim 18 wherein said methyl α-cyclohexyl-α-hydroxybenzeneacetate is predominantly of the S configuration and said desethyloxybutynin is S-desethyloxybutynin.

20. A pharmaceutical composition for treating urinary incontinence comprising (S)-desethyloxybutynin, or a pharmaceutically acceptable salt thereof, and a pharmaceutically acceptable carrier.

21. The pharmaceutical composition of claim 20 wherein the pharmaceutically acceptable carrier is a solid pharmaceutically acceptable carrier.

\* \* \* \* \*

UNITED STATES PATENT AND TRADEMARK OFFICE
CERTIFICATE OF CORRECTION

PATENT NO. : 5,677,346
DATED : October 14, 1997
INVENTOR(S) : Aberg et al.

Page 1 of 3

It is certified that error appears in the above-identified patent and that said Letters Patent is hereby corrected as shown below:

Scheme A at column 4:

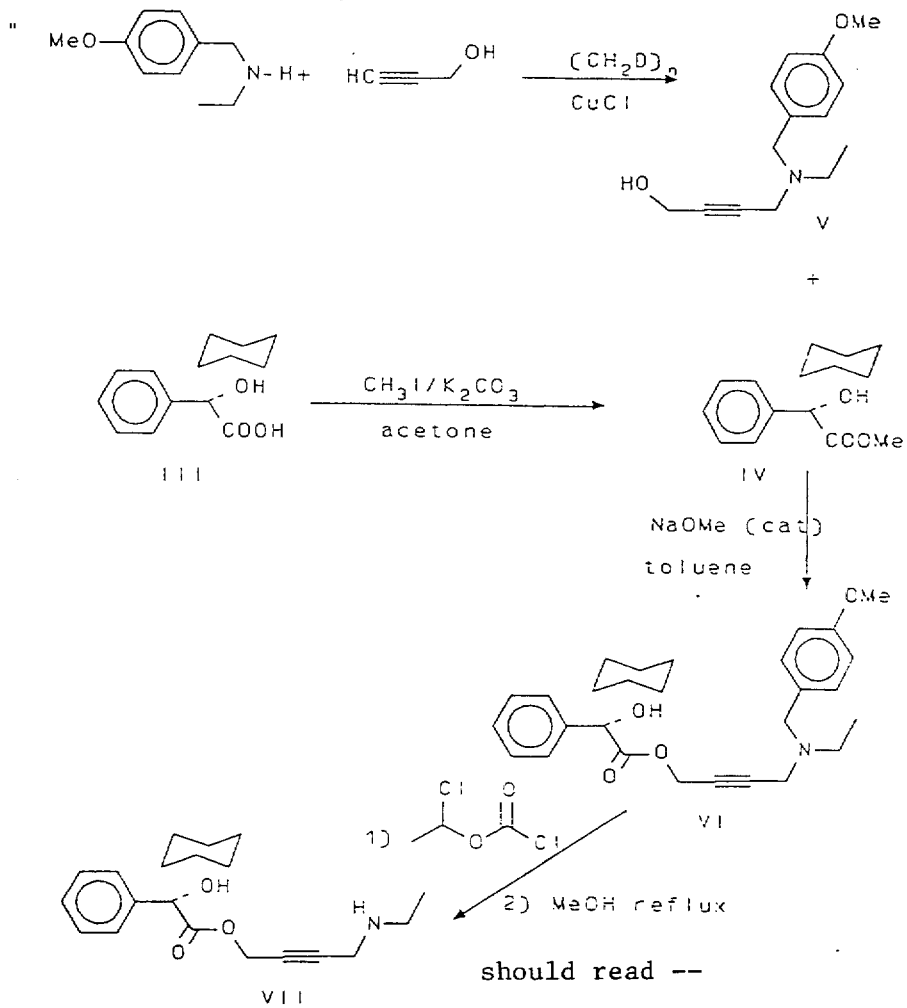

should read --

UNITED STATES PATENT AND TRADEMARK OFFICE
CERTIFICATE OF CORRECTION

PATENT NO. : 5,677,346

DATED : October 14, 1997

INVENTOR(S) : Aberg et al.

It is certified that error appears in the above-identified patent and that said Letters Patent is hereby corrected as shown below:

Scheme A

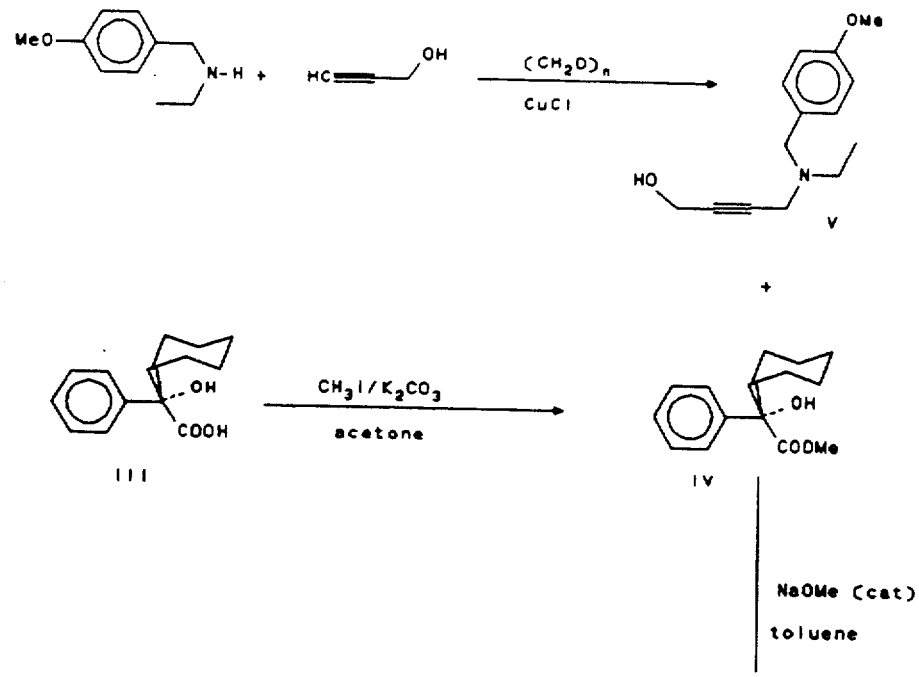

UNITED STATES PATENT AND TRADEMARK OFFICE
CERTIFICATE OF CORRECTION

PATENT NO. : 5,677,346

DATED : October 14, 1997

INVENTOR(S) : Aberg et al.

It is certified that error appears in the above-identified patent and that said Letters Patent is hereby corrected as shown below:

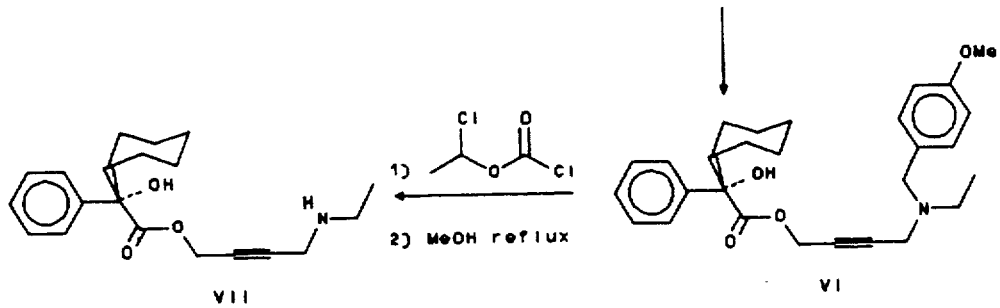

--.

Signed and Sealed this

Seventeenth Day of February, 1998

*Attest:*

BRUCE LEHMAN

*Attesting Officer*      *Commissioner of Patents and Trademarks*